United States Patent
Dillon et al.

(10) Patent No.: US 6,464,989 B2
(45) Date of Patent: *Oct. 15, 2002

(54) TEA TREE OIL EMULSION FORMULATIONS

(75) Inventors: Kathy Dillon; Kevin Korth, both of Idaho Falls; Becky Zehntner, Blackfoot; David Montgomery, Chubbuck, all of ID (US)

(73) Assignee: Melaleuca Incorporated, Idaho Falls, ID (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/303,311

(22) Filed: Apr. 30, 1999

(65) Prior Publication Data

US 2002/0001601 A1 Jan. 3, 2002

Related U.S. Application Data

(60) Provisional application No. 60/083,904, filed on May 1, 1998.

(51) Int. Cl.[7] .................................................. A61K 6/00
(52) U.S. Cl. ...................................................... 424/401
(58) Field of Search ................................ 424/401, 400, 424/405, 455; 264/4.1; 514/937, 938; 427/213.3

(56) References Cited

U.S. PATENT DOCUMENTS

| 5,455,033 | A | * | 10/1995 | Silverman et al. | 424/195 |
| 5,738,863 | A | * | 4/1998 | Sackin et al. | 424/405 |
| 5,744,062 | A | * | 4/1998 | Dahms et al. | 252/312 |
| 5,746,836 | A | * | 5/1998 | Fukai | 134/1 |
| 5,976,555 | A | * | 11/1999 | Liu et al. | 424/401 |
| 6,022,549 | A | * | 2/2000 | Dyer | 424/401 |
| 6,022,551 | A | * | 2/2000 | Jampani et al. | 424/405 |

* cited by examiner

*Primary Examiner*—Michael G. Hartley
(74) *Attorney, Agent, or Firm*—Fish & Richardson P.C., P.A.

(57) ABSTRACT

The invention provides a tea tree oil emulsion comprising tea tree oil at a concentration of greater than about 20% on a weight by weight basis, an emulsifier, and a wherein the emulsion remains stable when packaged in a flexible tube. A method for producing the tea tree oil emulsion and an article of manufacture containing the tea tree oil emulsion is also provided.

3 Claims, No Drawings

TEA TREE OIL EMULSION FORMULATIONS

This application claims the benefit of prior U.S. provisional application 60/083,904 filed May 1, 1998.

FIELD OF THE INVENTION

The invention relates to emulsions containing Tea Tree Oil.

BACKGROUND OF THE INVENTION

Tea Tree Oil (TTO) is isolated by distilling the oil contained in the stems and leaves of the paperbark tree *Melaleuca alternafolia*. TTO has unique medicinal properties including antimicrobial and antifungal characteristics. Additionally, TTO provides a soothing sensation when in contact with a person's skin. When applied as a neat oil, however, TTO quickly evaporates diminishing its effects. To prolong its effects, it is desirable to apply TTO in a form that will both remain in contact with the skin and deliver the highest concentration of TTO possible.

Medicaments, such as the original Melan-Gel(™) formulation, containing TTO are typically packaged in plastic or glass jars. Opening and closing such containers exposes a relatively large surface area of the medicament to air, which provides an opportunity for evaporation of the TTO. Furthermore, repeated exposure of the medicament to air can facilitate oxidation of some of the chemical components of the medicament. Oxidation can change the chemical makeup of the medicament, which may affect the medicament's effectiveness.

TTO can be administered as a gel suspension. At high TTO concentrations, however, TTO tends to separate from the gel base formula, corrupting the gel suspension. Moreover, changes in temperature and/or applying physical shear forces, such as kneading a gel suspension, tend to accentuate the separation difficulties attributed to TTO. Thus, it is difficult to suspend high concentrations of TTO in gel or waxy base formula because as the TTO concentration increases it tends to thin the wax base.

As such, currently known TTO formulations containing higher concentrations of TTO will separate into their base ingredients when the gel is packaged in a flexible tube. In contrast, current TTO formulations are stable when packaged in glass or plastic jars or small bottles. These formulations are referred to as "jar" formulations. It is thought that since the wax matrix sets up in a jar it prevents TTO from separating out of the wax matrix. In addition, TTO evaporates more quickly when packaged in a jar as opposed to a tube due to the larger exposed surface area and the lack of an air tight lid seal on jars after they are first opened. Accordingly, it is currently impractical to offer TTO formulations in tightly sealed containers and/or flexible tubes.

SUMMARY OF THE INVENTION

The present invention involves the discovery that the certain combinations of tea tree oil and emulsifiers produce a tea tree oil emulsion or tea tree oil composition that remains stable. The combinations can contain waxes, oils, emulsifiers, and TTO among other ingredients. The present invention further involves a method for producing such a tea tree oil emulsion and an article of manufacture containing the emulsion.

In one aspect, the invention features a tea tree oil emulsion including tea tree oil at a concentration greater than about 20% on a weight by weight basis, an emulsifier, and a wax. Such an emulsion or composition can be stable at room temperature. In some embodiments, the TTO emulsion or composition is visually stable.

In another embodiment, the emulsion also contains wheat germ oil and/or including pentaerythritol ether. The pentaerythritol ether may be at a concentration ranging from about 15% to about 25% on a weight by weight basis.

The tea tree oil concentration can be increased to any concentration above 20% including at least about 22, 23, 24, 25, 26, 27, 28, 29, or 30 percent on a weight by weight basis. In certain embodiments, the tea tree oil is of a pharmaceutical grade tea tree oil. As such, the tea tree oil may have a terpenene-4-ol concentration greater than about 36% and a cineol concentration less than about 7%.

In other embodiments, the emulsifier is at a concentration less than about 25% on a weight by weight basis, ranges from about 0.5% to about 23% on a weight by weight basis, ranges from about 0.5% to about 10% on a weight by weight basis, or is at a concentration of about 9% on a weight by weight basis. Useful emulsifiers may be used alone or in combination and may be selected from the group consisting of stearic acid, glyceryl stearate, polyethyleneglycol 100 stearate, steareth-21, polyoxyethylene(2) stearyl ether, steareth-2, polysorbate 20, cetearyl alcohol, and polysorbate 60. Glyceryl stearate and polyethyleneglycol 100 stearate may be also used alone or in combination as a blend. Other emulsifiers may also be blended.

In some embodiments, the emulsifiers are used in combination and may be at concentrations where stearic acid is at a concentration concentrations ranging from about 3% to about 8% on a weight by weight basis, glyceryl stearate and polyethylene glycol 100 stearate are at a concentration ranging from about 1% to about 5% on a weight by weight basis, steareth-21 is at a concentration ranging from about 0.5% to about 5.0% on a weight by weight basis, and steareth-2 is at a concentration ranging from about 0.5% to about 5.0% on a weight by weight basis.

In other embodiments, the TTO emulsion includes wheat germ oil, cocoa butter, beeswax, ozokerite wax, pentaerythritol ether, vitamin E acetate, vitamin A, and vitamin D3. These additional substances may be used alone or in combination. For example, the wheat germ oil concentration can range from about 15% to 25%, the cocoa butter concentration can range from about 15% to about 25%, the, beeswax concentration can range from about 3% to about 8%, the ozokerite wax concentration can range from about 1% to about 5%, the pentaerythritol ether can range from about 15% to about 25%, the vitamin E acetate concentration can range from about 0.1% to about 2%, the vitamin A concentration can range from about 0.1% to about 2 percent, the vitamin D concentration can range from about 0.1% to about 2 percent. In other embodiments, the emulsifier concentration ranges from about 0.5% to about 23%.

In other embodiments, the TTO emulsion has a shelf life of 1 year, 18 months, 2 years, or more.

In another aspect, the invention features, a method for producing a tea tree oil emulsion including the steps of: a) mixing and heating an emulsifier and a wax to a temperature effective for dissolving the emulsifier and the wax thereby forming an emulsifier and wax combination; b) cooling the combination; c) adding tea tree oil to the cooled combination to form a tea tree oil mixture; and d) emulsifying the mixture forming a tea tree emulsion, the emulsion having a tea tree oil concentration of at least about 20% on a weight by weight basis, the emulsion being stable at room temperature.

In other embodiments, the heating step of the method includes heating the emulsifier and the wax to a temperature of about 80° C. Also, the method can include cooling the combination to a temperature of about 70° C. The heating and cooling steps can be used together in a single method. In other embodiments, a second emulsifier is added to the combination after the cooling step. The second emulsifier can be a blend of glyceryl stearate and polyethylene glycol 100 stearate.

In another aspect, the invention features an article of manufacture including a tea tree oil emulsion including a tea tree oil concentration greater than about 20% on a weight by weight basis, an emulsifier, and a wax, the emulsion packaged in a flexible container suitable for dispensing the tea tree oil emulsion, the emulsion remaining stable while contained within the flexible container. In some embodiments, the article of manufacture may reduce TTO exaporation and/or oxidation of the ingredients. The article of manufacture can be used with any of the mentioned TTO emulsion embodiments disclosed herein.

Advantages of the invention include being able to package a TTO emulsion or composition in a flexible tube wherein the TTO emulsion remains stable in the flexible tube. Stable TTO emulsions can then be dispensed from a flexible tube as unfractionated, and thus uniform, dosages of TTO. Accordingly, the TTO emulsions or compositions of the present invention can be stored and dispensed from flexible tubes without undergoing visual separation of the oil and wax constituents. Storing the TTO compositions in this manner may also reduce evaporation and/or oxidation of the TTO composition.

Unless otherwise defined, all technical and scientific terms and abbreviations used herein have the same meaning as commonly understood by one of ordinary skill in the art to which this invention pertains. Although methods and materials similar or equivalent to those described herein can be used in the practice of the invention, suitable methods and materials are described below. All publication, patent applications, patents and other references mentioned herein are incorporated by reference in their entirety. In case of conflict, the present specification, including definitions, will control. Other features and advantages of the invention will be apparent from the following detailed description and from the claims.

DESCRIPTION OF THE PREFERRED EMBODIMENTS

The present invention involves the discovery that the certain combinations of tea tree oil and emulsifiers produce a tea tree oil emulsion or composition (TTO emulsion) that remains stable. Accordingly, the TTO emulsion may contain waxes, oils, emulsifiers among other ingredients to form a non-aqueous, viscous TTO-containing composition that resists separation under daily use conditions when packaged in a flexible tube. The present invention further involves a method for producing such a TTO emulsion and an article of manufacture containing the emulsion.

Medicaments such as the original Mela-Gel(™) formulation containing TTO are packaged in plastic or glass jars. It was observed that the TTO evaporates over time when packaged in such a container. The inventors hypothesized that Mela-Gel(™) in a flexible tube would diminish TTO loss due to evaporation. However, when known formulations of Mela-Gel(™) were packaged in tubes, the TTO would separate from its wax matrix when subjected to the rigors of everyday use by the typical consumer.

Due to the convenience of dispensing medicaments in flexible tubes and the desire to maintain TTO at the highest concentration possible, it was hypothesized that it would be useful to formulate TTO in a wax/petrolatum based emulsion that would be suitable for storing and dispensing TTO in a flexible tube. The present inventors have discovered such an emulsion. This TTO emulsion and a process for preparing it are described and claimed herein.

In a first embodiment, the invention provides a TTO emulsion containing TTO at a concentration greater than about 20% on a weight by weight basis (w/w) and an emulsifier source. Preferably the TTO is at a concentration of about 23% w/w or more.

TTO is defined by the International Standards Organization monograph ISO 4730. TTO from any source can be used in the present invention provided that the TTO meets the specifications defined in ISO 4730. Commercial suppliers of TTO are known. Preferably the TTO is of a pharmaceutical grade, which is defined as having a terpenene-4-ol concentration greater than about 36% and a cineol concentration less than about 7%.

The emulsifier source may contain one or more emulsifiers and may include synthetic or natural occurring emulsifiers. Illustrative examples of useful emulsifiers include known emulsifiers used for preparing ointments, emulsifiers commonly used in pharmaceuticals, and emulsifiers used in cosmetics. Preferred emulsifiers include stearic acid, a blend of glyceryl stearate and polyethyleneglycol 100 stearate (PEG 100 stearate), Brij(™) 721 (steareth-21), Brij(™) 72 (polyoxyethylene(2) stearyl ether or steareth-2), polysorbate 20, cetearyl alcohol, polysorbate 60, and other similar emulsifiers. Preferably, the emulsifier source is a combination of the emulsifiers stearic acid at 3–8% w/w, glyceryl stearate & PEG 100 stearate at 1–5% w/w, steareth-21 at 0.5–5.0% w/w, and steareth-2 at 0.5–5.0% w/w.

Typically, the TTO emulsion also contains ingredients found in known TTO medicaments such as wheat germ oil, cocoa butter, beeswax, ozokerite wax, pentaerythritol ether (PPG 1–5), vitamin E acetate (dl-Alpha tocopheryl acetate), vitamin A, vitamin D3 and other similar substances. It is to be understood that other known waxes and similar substances that are useful for producing medicaments and cosmetics may also be useful in the present invention. Altering the percentage of waxes and oils other than the TTO may affect the consistency of the TTO emulsion.

A preferred TTO emulsion includes the indicated ingredients within the following ranges.

| Ingredient | w/w | (preferred %) |
|---|---|---|
| Wheat Germ Oil | 15–25% | (18–20%) |
| Cocoa Butter (deodorized) | 15–25% | (18–20%) |
| Beeswax | 3–8% | (4.5%) |
| Ozokerite Wax | 1–5% | (2.5%) |
| Stearic Acid XXX | 3–8% | (4.5–6.5%) |
| Glyceryl Stearate & PEG 100 Stearate | 1–5% | (2.5%) |
| Steareth-21 | 0.5–5.0% | (1–2%) |
| Steareth-2 | 0.5–5.0% | (1–2%) |
| PPG 1-5 | 15–25% | (20%) |
| Vitamin E Acetate (USP or cosmetic grade) | 0.1–2.0% | (0.9%) |
| Vitamin A & D3 5:1 (blend) | 0.1–2.0% | (0.1%) |
| Tea Tree Oil (USP) | 20–30% | (23%) |
| TOTAL | 100% | 100% |

Each ingredient found in the preferred TTO emulsion is commercially available. A preferred stearic acid is triplepressed, non-food grade, and kosher approved. A preferred stearic acid is available from Polyesther Corporation, P.O. Drawer 5076, Southhampton, N.Y., 11969-5076. A preferred blend of glyceryl stearate & PEG 100 stearate is available from R.I.T.A. Corporation, P.O. Box 1487, Woodstock, Ill. 60098. PPG 1–5 is available from Phillip Rockley, Ltd., 11 Technology Drive, East Setauket, N.Y. 11733.

In another embodiment, the invention provides a method for preparing a TTO emulsion containing TTO at a concentration of at least 20% w/w and further containing an emulsifier source.

To practice the described methods, a combination of emulsifiers and other ingredients are heated to 80° C. while mixing the combination at medium speed (21 r.p.m.). The stirring is continued until all the ingredients are completely dissolved. The other ingredients included in the first step may include PPG 1–5, cocoa butter, beeswax, ozokerite wax, stearic acid, steareth-2, steareth-21 and the blend of glyceryl stearate and PEG 100 stearate.

The combination is cooled to less than or equal to about 50° C. while continuing the mixing process. Preferably, the temperature is between about 45–50° C. As the combination cools to less than about 50° C., additional ingredients, which may include wheat germ oil, vitamin E acetate, the vitamin A & D3 blend, the blend of glyceryl stearate and PEG 100 stearate, and TTO are added to the combination. The vitamins and/or TTO may tend to evaporate if added to the mixture at temperatures higher than about 50° C. Thus, it may be necessary to delay adding the vitamins and TTO until the combination reaches a temperature of less than or equal to about 50° C.

After the additional ingredients are added, the resulting mixture is emulsified (3450 r.p.m. in a rotostat) in the mixer for 1–2 additional minutes and then mixed at medium speed for an additional 15 minutes.

Another illustrative method proceeds as follows. A combination of emulsifiers and other ingredients are heated to 80° C. while mixing the combination at medium speed (21 r.p.m.). The stirring is continued until all the ingredients are completely dissolved. The other ingredients included in the first step may include PPG 1–5, cocoa butter, beeswax, ozokerite wax, stearic acid, steareth-2, steareth-21, wheat germ oil, and the blend of glyceryl stearate and PEG 100 stearate.

The combination is cooled to less than or equal to about 50° C. while continuing the mixing process. Preferably, the temperature is between about 45–50° C. As the combination cools to less than about 50° C., additional ingredients, which may include vitamin E acetate, the vitamin A & D3 blend, and TTO are added to the combination.

Alternatively, another illustrative method proceeds as follows. A combination of emulsifiers and other ingredients are heated to 80° C. while mixing the combination at medium speed (21 r.p.m.). The stirring is continued until all the ingredients are completely dissolved. The other ingredients included in the first step may include PPG 1–5, cocoa butter, beeswax, ozokerite wax, stearic acid, steareth-2, steareth-21, and the blend of glyceryl stearate and PEG 100 stearate.

The combination is cooled to less than or equal to about 70° C. while continuing the mixing process. At about 70° C., additional ingredients, which may include vitamin E acetate, wheat germ oil, the vitamin A & D3 blend, and TTO are added to the combination.

After the additional ingredients are added, the resulting mixture is emulsified (3450 r.p.m. in a rotostat) in the mixer for 1–2 additional minutes and then mixed at medium speed for an additional 15 minutes.

After emulsification, the TTO emulsion can be dispensed into flexible tubes without further mixing using known methods. When dispensed, the TTO emulsion temperature should be maintained between 50–70° C., preferably between 60–65° C., also preferably at about 65° C. without further mixing. The filled tube may be crimped immediately. The crimped tube should be allowed to reach room or ambient temperature slowly prior to use to ensure that the TTO emulsion does not separate. An illustrative example of slow cooling is to place a tube containing the TTO emulsion (55–65° C.) at room temperature and allow the tube to cool without further assistance.

It is to be understood that other than the TTO and vitamins, which may be susceptible to evaporation at temperatures higher than about 50° C., the order of adding the ingredients is not considered critical to the invention. As such, alternative methods for adding the other ingredients are within the scope of the claimed invention.

It is also apparent that the TTO emulsion described herein is not limited to being dispensed from sealable tubes. To the contrary, the TTO emulsion may be packaged in and/or dispensed from any acceptable container. Illustrative examples of acceptable containers include known jars, bottles, sealable or nonsealable tubes, and other similar containers that are useful for packaging or dispensing medicinal ointments or emulsions. These containers may be made from any acceptable material including glass, plastic and metal.

One unique feature of the TTO emulsions and methods for producing TTO emulsions that are described and claimed herein is that the TTO emulsion remains stable when packaged in a flexible tube. Further, TTO emulsions of the invention retain the aesthetic properties that are associated with known TTO medicants. These features attributed to useful TTO emulsions of the invention prevent the loss of TTO due to evaporation and/or oxidation and provide a convenient method for packaging TTO medicants.

A stable TTO emulsion is an emulsion wherein the TTO does not separate from the emulsifier source when the TTO emulsion is initially cooled to room temperature. Useful, TTO emulsions in accordance with this invention remain stable as long as they retain a majority of their aesthetic properties. TTO emulsion aesthetic properties include the color, odor, melting point, visual stability, and TTO oil concentration of the TTO emulsion. The principal concern is that the TTO emulsion retains its visual stability. A TTO emulsion may be considered visually stable as long as the TTO emulsion can be dispensed unfractionated thereby dispensing a uniform dosage of the TTO emulsion. A unstable TTO emulsion may separate into its individual ingredients and may produce an oily product when dispensed. Preferably, the TTO emulsion remains stable for 2 years.

The visual stability of a TTO emulsion can be evaluated using known methods. An illustrative method for evaluating the visual stability of a TTO emulsion includes allowing an evaluating panel of people use the TTO emulsion packaged in a flexible tube. Such tests will identify TTO emulsions that do not withstand the kneading and temperature variations associated with everyday use. For example, TTO emulsions packaged in flexible tubes are given to an evaluating panel. The panel members are told to use the products for a few days. A TTO emulsion that retains its aesthetic properties following a few days of everyday use passes the evaluating panel test. TTO emulsions that do not pass the consumer test typically result in TTO separating from the wax matrix, which causes the TTO to exit the flexible tube as an oil. Known jar TTO formulations do not pass the evaluating panel test. It is apparent, however, that additional or alternative mechanical kneading or physical shear force analyses may be performed using known techniques for evaluating the stability of conventional emulsions or ointments.

Another method for evaluating the stability of a TTO emulsion includes subjecting the emulsion to accelerated time, temperature and humidity conditions. Typically, packaged TTO emulsions are placed in a chamber maintained at 40° C. and 75% humidity. These conditions can be achieved using a Sure-Temp temperature and humidity controlled chamber. A 2 month accelerated time, temperature and humidity test correlates to 18 month room temperature stability and allows the TTO emulsion product to have an expiration date of 18 months. A 3 month or 90 day accelerated time, temperature and humidity test correlates to 24 month room temperature stability and allows the TTO emulsion product to have an expiration date of 24 months. Following each humidity test samples can be evaluated for color, odor, melting point, appearance and visual stability by a quality control technician.

The visual stability can be assessed by squeezing a sample of the TTO emulsion out of the tube to see if any separated TTO comes out. This same sample is then cut open and inspected for signs of separation. Signs of separation may include one phase oiling out of the emulsion, the appearance of liquids within a solid, the appearance of solid particles, lumps and other similar signs that would be apparent to someone of ordinary skill in the art of emulsions. Known jar TTO formulations packaged in flexible tubes can pass the accelerated time, temperature and humidity test.

The color of a TTO emulsion can be analyzed using the Pantone Matching System(™) (1-888-pantone). Typically, the color of the preferred TTO emulsion matches color standard 459U. Acceptable color variations include 458U and 460U, which are slightly darker or lighter than 459U, respectively.

Acceptable odors for TTO medicants are known. Typically, the TTO emulsion contains an odor characteristic of medicants containing tea tree oil. Acceptable melting temperature for the preferred TTO emulsions are between about 45–55° C.

Visual appearance or consistency of the TTO emulsion is an important factor. Acceptable TTO emulsions appear to the naked eyes to be one phase with little or no oiling out of TTO. Acceptable TTO emulsion should not appear to have liquids within a solid matrix or have noticeable solid particles, lumps, or oil pockets within the TTO emulsion.

To determine the TTO concentration in a TTO emulsion, samples can be analyzed by known gas chromatography techniques. For example, samples can be sent to the Biopharmaceutical Analysis Laboratory, Department of Pharmaceutical Sciences, College of Pharmacy at Idaho State University.

In another aspect of the invention, an article of manufacture containing a TTO emulsion containing TTO at a concentration of at least 20% w/w and an emulsifier is provided. The article is contained within a packaging material that is labeled to indicate that the emulsion is useful for medicinal purposes. Any common packaging, manufacturing or printing methods can be used to prepare the article of manufacture. Preferably the article of manufacture consists of a flexible sealable tube. Methods to manufacture and fill sealable tubes are known. These types of tubes include tubes used to dispense medical ointments and toothpaste.

The invention will be further understood with reference to the following illustrative embodiments, which are purely exemplary, and should not be taken as limiting the true scope of the present invention as described by the claims.

EXAMPLE 1

Tube Dispensable Mela-Gel (TM)
When combined according to the methods described herein, the ingredients designated below formed a TTO emulsion that was stable when packaged in a flexible tube.

| Ingredient | w/w | Weight |
| --- | --- | --- |
| Wheat Germ Oil | 20% | 180.0 g |
| Cocoa Butter (deodorized) | 20% | 180.0 g |
| Beeswax | 4.5% | 40.5 g |
| Ozokerite Wax | 2.5% | 22.5 g |
| Stearic Acid XXX | 4.5% | 40.5 g |
| Glyceryl Stearate & PEG 100 Stearate | 2.5% | 22.5 g |
| Steareth-21 | 1.0% | 9.0 g |
| Steareth-2 | 1.0% | 9.0 g |
| PPG 1-5 | 20% | 180.0 g |
| Vitamin E Acetate | 0.9% | 8.1 g |
| Vitamin A & D3 5:1 (blend) | 0.1% | 0.9 g |
| Tea Tree Oil (pharmaceutical grade) | 23% | 207.0 g |
| TOTAL | 100% | 900 g |

EXAMPLE 2

Preparing Tube Dispensable Mela-Gel(™)

The measured ingredients in Example 1 were combined according to the following procedure. The aliquots of PPG 1–5, Cocoa Butter, Beeswax, Ozokerite Wax, Stearic acid, Steareth-2, and Steareth-21 were added to a heatable mixing processor. The mixer was then heated to 80° C. while mixing at 21 r.p.m. The ingredients were mixed at medium speed until the ingredients were completely dissolved.

After dissolving the initial ingredients, the mixture was cooled to 45° C. While the mixture cooled the blend of Glyceryl Stearate and PEG 100 stearate was added to the mixture. After the mixture reached 45° C., aliquots of wheat germ oil, vitamin E acetate, vitamin A & D3, and TTO were added to the mixture. This mixture was then emulsified at 3450 r.p.m. for 1–2 minutes. The mixture was mixed at 21 r.p.m. for an additional 15 minutes.

The resulting TTO emulsion was packaged into flexible tubes without further mixing. At this time, the TTO emulsion temperature was maintained at 45–60° C. without further mixing. The tube was crimped immediately after being filled, placed at room temperature and allowed to cool to ambient temperature prior to use. The TTO emulsion retained its aesthetic properties and the TTO did not separate from the emulsifier matrix.

The TTO emulsion retained its aesthetic properties when analyzed by an evaluating panel, i.e., the emulsions did not show any sign of separation during daily use of the emulsion. Samples of the TTO emulsion were evaluated at 40° C. and 75% humidity in a Sure-Temp controlled temperature and humidity chamber. The samples remained stable after 2 months exposure. Additional samples remained in the Sure-Temp chamber to be evaluated after a four month exposure.

EXAMPLE 3

Tube Dispensable Mela-Gel (TM)
When combined according to the methods described herein, the ingredients designated below formed a TTO emulsion that was stable when packaged in a flexible tube.

| Ingredient | w/w | Weight |
|---|---|---|
| Wheat Germ Oil | 18% | 162.0 g |
| Cocoa Butter (deodorized) | 18% | 162.0 g |
| Beeswax | 4.5% | 40.5 g |
| Ozokerite Wax | 2.5% | 22.5 g |
| Stearic Acid XXX | 6.5% | 58.5 g |
| Glyceryl Stearate & PEG 100 Stearate | 2.5% | 22.5 g |
| Steareth-21 | 2.0% | 18.0 g |
| Steareth-2 | 2.0% | 18.0 g |
| PPG 1-5 | 20% | 180.0 g |
| Vitamin E Acetate | 0.9% | 8.1 g |
| Vitamin A & D3 5:1 (blend) | 0.1% | 0.9 g |
| Tea Tree Oil (pharmaceutical grade) | 23% | 207.0 g |
| TOTAL | 100% | 900 g |

EXAMPLE 4

Preparing Tube Dispensable Mela-Gel(™)

The ingredients in Example 3 were combined according to the method described in Example 2 to produce a TTO emulsion that was stable when packaged in a flexible tube.

The TTO emulsion retained its aesthetic properties when analyzed by an evaluating panel, i.e., The emulsions did not show any sign of separation during daily use of the emulsion. Samples of the TTO emulsion were evaluated at 40° C. and 75% humidity in a Sure-Temp controlled temperature and humidity chamber. The samples remained stable after 2 months exposure. Additional samples remained in the Sure-Temp chamber to be evaluated after a four month exposure.

EXAMPLE 5

Stability Evaluation

The ingredients in Example 3 were combined according to the percentages indicated in Example 3. The ingredients were combined according to the methods described herein to produce a TTO emulsion that was stable when packaged in a flexible tube (Lot #1). Briefly, PPG 1–5, cocoa butter, beeswax, ozokerite wax, stearic acid, steareth-2, steareth-21, and glyceryl stearate & PEG-100 stearate were combined and heated to 80° C. while mixing to dissolve and/or melt the ingredients to form a combination. The combination was cooled to 70° C. During the cooling period wheat germ oil, vitamin E acetate, and the vitamin A & D3 blend was added to the combination. At 70° C., the tea tree oil was added to form a mixture. The mixture was emulsified for 1–2 minutes and then mixed for an additional 15 minutes. The resulting TTO emulsion was packaged at a temperature of about 65° C. The above procedure was repeated to produce a second TTO emulsion that was stable when packaged in a flexible tube (Lot #2). Each tube was weighed and recorded. A sample from each lot was tested after dispensing the formulations. At the initial time point (Interval 0), the container, cap, and label seal of the flexible tubes containing the TTO emulsions for Lots #1 and #2 were intact. The color, odor, and appearance of the TTO emulsions were evaluated to see if the test samples matched the standard and if so are designated TMS. The melting point of Lot #1 was 42° C. and the TTO concentration was 23.60% on a weight by weight basis. The melting point of Lot#2 was 44° C. and the TTO concentration was 23.83% on a weight by weight basis.

Samples of Lots #1 & #2 were further evaluated according to the methods described herein. The evaluation methods included storing samples at 40° C. and 75% relative humidity in a Sure-Temp controlled temperature and humidity chamber for 30, 60, 90, and 120 days. Other samples were stored at temperatures ranging from 2–8° C. for one week. Other samples were subjected to repeated freeze thaw cycles by cooling samples below −18° C. for 23 hours then defrosting the samples by raising the temperature above 0° C. The defrost cycles lasted about 1 hour and occurred once per 24 hour freeze period. Freezer samples were tested after 48 hours in the freezer. The results of sample testing for Lots #1 and #2 are reported below in Table 1 and Table 2, respectively.

TABLE 1

Lot #1 Stability Testing

| Interval | 0 | <−18° C. | 2–8° C. | 30 Days | 60 Days | 90 Days | 120 Days |
|---|---|---|---|---|---|---|---|
| Container Integrity | OK | OK | OK | OK | OK | OK | OK |
| Closure/Cap Integrity | OK | OK | OK | OK | OK | OK | OK |
| Label/Seal Integrity | OK | OK | OK | OK | OK | OK | OK |
| Gross Wt. Change (g) | 0.000 | 0.000 | 0.001 | 0.026 | 0.069 | 0.025 | 0.031 |
| Color | TMS | TMS | TMS | TMS | TMS | TMS | TMS |
| Odor | TMS | TMS | TMS | TMS | TMS | TMS | TMS |
| Appearance | TMS | TMS | TMS | TMS | TMS | TMS | TMS |
| Melting Point (C. °) | 42 | 42 | 44 | 48 | 42 | 40 | 42 |
| Melaleuca Oil Concentration (%) | 23.60 | 23.61 | 23.68 | 23.76 | 23.71 | 25.25 | 23.80 |

TABLE 2

Lot #2 Stability Testing

| Interval | 0 | <−18° C. | 2–8° C. | 30 Days | 60 Days | 90 Days | 120 Days |
|---|---|---|---|---|---|---|---|
| Container Integrity | OK | OK | OK | OK | OK | OK | OK |
| Closure/Cap Integrity | OK | OK | OK | OK | OK | OK | OK |
| Label/Seal Integrity | OK | OK | OK | OK | OK | OK | OK |
| Gross Wt. Change (g) | 0.002 | 0.000 | 0.004 | 0.029 | 0.031 | 0.027 | 0.040 |
| Color | TMS | TMS | TMS | TMS | TMS | TMS | TMS |
| Odor | TMS | TMS | TMS | TMS | TMS | TMS | TMS |
| Appearance | TMS | TMS | TMS | TMS | TMS | TMS | TMS |
| Melting Point (C. °) | 44 | 48 | 45 | 47 | 36 | 42 | 42 |
| Melaleuca Oil Concentration (%) | 23.83 | 23.57 | 23.71 | 24.04 | 23.93 | 25.07 | 23.29 |

Statistical analysis of the resulting data, including a T-test evaluation, was conducted according to conventional statistical methods using the computer program statistica (V. 5.1 Stasoft). The results are shown below in Tables 3–5. A p-value less than 0.05 is statistically significant and would indicate the possibility of outliers in a dataset. All datasets had p values greater than 0.05 and thus indicated that the datasets did not contain outliers.

TABLE 3

T-test for Gross Container Weight Change

STAT. BASIC STATS — T-test for Independent samples
Note: Variables were treated as independent samples

| Group 1 vs. Group 2 | Mean Group 1 | Mean Group 2 | t-value | df | p | Valid N Group 1 |
|---|---|---|---|---|---|---|
| Lot #1 vs. Lot #2 | .021714 | .019000 | .240551 | 12 | .813963 | 7 |

| Group 1 vs. Group 2 | Valid N Group 2 | Std. Dev. Group 1 | Std. Dev. Group 2 | F-ratio variances | p variances |
|---|---|---|---|---|---|
| Lot #1 vs. Lot #2 | 7 | .024911 | .016452 | 2.292752 | .336012 |

TABLE 4

T-test for Melting Point

STAT BASIC STATS — T-test for Independent samples
Note: Variables were treated as independent samples

| Group 1 vs. Group 2 | Mean Group 1 | Mean Group 2 | t-value | df | p | Valid N Group 1 |
|---|---|---|---|---|---|---|
| Lot #1 vs. Lot #2 | 42.85714 | 43.42857 | −.319235 | 12 | .755037 | 7 |

| Group 1 vs. Group 2 | Valid N Group 2 | Std. Dev. Group 1 | Std. Dev. Group 2 | F-ratio variances | p variances |
|---|---|---|---|---|---|
| Lot #1 vs. Lot #2 | 7 | 2.544836 | 3.994043 | 2.463235 | .297031 |

TABLE 5

T-test for % Tea Tree Oil in TTO Emulsion

STAT BASIC STATS — T-test for Independent samples
Note: Variables were treated as independent samples

| Group 1 vs. Group 2 | Mean Group 1 | Mean Group 2 | t-value | df | p | Valid N Group 1 |
|---|---|---|---|---|---|---|
| Lot #1 vs. Lot #2 | 23.91573 | 23.92000 | −.013857 | 12 | .989172 | 7 |

| Group 1 vs. Group 2 | Valid N Group 2 | Std. Dev. Group 1 | Std. Dev. Group 2 | F-ratio variances | p variances |
|---|---|---|---|---|---|
| Lot #1 vs. Lot #2 | 7 | .592870 | .564004 | 1.104983 | .906642 |

Other aspects, advantages, and modifications are within the scope of the following claims.

What is claimed is:

1. A tea tree emulsion comprising tea tree oil at a concentration greater than about 22% on a weight by weight basis, an emulsifier, wheat germ oil, cocoa butter, beeswax, ozokerite wax, pentaerythritol ether, vitamin E acetate, vitamin A, and vitamin D3, said emulsion being stable at room temperature.

2. The emulsion of claim 1 wherein said wheat germ oil concentration ranges from about 15% to 25%, said cocoa butter concentration ranges from about 15% to about 25%, said, beeswax concentration ranges from about 3% to about 8%, said ozokerite wax concentration ranges from about 1% to about 5%, said pentaerythritol ether ranges from about 15% to about 25%, said vitamin E acetate concentration ranges from about 0.1% to about 2%, said vitamin A concentration ranges from about 0.1% to about 2percent, said vitamin D3 concentration ranges from about 0.1% to about 2 percent, and said emulsifier concentration ranges from about 0.5% to about 23%.

3. The emulsion of claim 2 wherein said emulsifier comprises a combination of stearic acid, glyceryl stearate, polyethylene glycol 100 stearate, steareth-21, and steareth-2.

* * * * *

UNITED STATES PATENT AND TRADEMARK OFFICE
CERTIFICATE OF CORRECTION

PATENT NO.    : 6,464,989 B2
DATED         : October 15, 2002
INVENTOR(S)   : Kathy Dillon et al.

It is certified that error appears in the above-identified patent and that said Letters Patent is hereby corrected as shown below:

<u>Title page,</u>
Item [57], ABSTRACT,
Line 3, after the second occurrence of "a" please insert -- wax --.

Signed and Sealed this

Fourth Day of March, 2003

Attest:

JAMES E. ROGAN
Attesting Officer    Director of the United States Patent and Trademark Office